United States Patent [19]
Miller et al.

[11] Patent Number: 5,332,398
[45] Date of Patent: Jul. 26, 1994

[54] INTRAMEDULLARY CATHETER
[75] Inventors: Larry J. Miller, Spring Branch; Ruben Zamorano-Gamez, San Antonio, both of Tex.
[73] Assignee: Board of Regents, The University of Texas System, Austin, Tex.
[21] Appl. No.: 866,992
[22] Filed: Apr. 10, 1992

Related U.S. Application Data

[62] Division of Ser. No. 648,624, Feb. 1, 1991, Pat. No. 5,122,114.
[51] Int. Cl.$^5$ ............................................. A61M 5/32
[52] U.S. Cl. .................................................. 604/175
[58] Field of Search .................. 604/93, 175, 174, 264, 604/272; 606/60, 62, 65, 72, 73

[56] References Cited

U.S. PATENT DOCUMENTS

| | | |
|---|---|---|
| 2,426,535 | 8/1947 | Turkel . |
| 3,310,051 | 3/1967 | Schulte . |
| 3,750,667 | 8/1973 | Pschenichny et al. . |
| 3,752,162 | 8/1973 | Newash . |
| 3,821,956 | 7/1974 | Gordhamer ...................... 604/264 X |
| 3,853,127 | 12/1974 | Spademan . |
| 4,011,602 | 3/1977 | Rybicki et al. ...................... 606/72 X |
| 4,177,814 | 12/1979 | Knepshield et al. . |
| 4,261,357 | 4/1981 | Kontos . |
| 4,400,169 | 8/1983 | Stephen . |
| 4,413,985 | 11/1983 | Wellner et al. . |
| 4,490,137 | 12/1984 | Moukheibir . |
| 4,491,126 | 1/1985 | Cullor . |
| 4,494,535 | 1/1985 | Haig . |
| 4,713,402 | 12/1987 | Solomon ........................... 604/96 X |
| 4,772,261 | 9/1988 | Von Hoff et al. . |
| 4,830,000 | 5/1989 | Shutt . |
| 4,969,870 | 11/1990 | Kramer et al. . |
| 5,098,977 | 3/1992 | Frautschi et al. ................. 604/96 X |
| 5,120,221 | 6/1992 | Orenstein et al. . |
| 5,167,960 | 12/1992 | Ito et al. .......................... 604/266 X |

FOREIGN PATENT DOCUMENTS

| | | |
|---|---|---|
| 0103081 | 3/1984 | European Pat. Off. . |
| 0134745 | 3/1985 | European Pat. Off. . |
| 2205314 | 8/1973 | Fed. Rep. of Germany . |
| 2834156 | 2/1980 | Fed. Rep. of Germany . |
| 88/00122 | 2/1988 | PCT Int'l Appl. . |
| US88/02391 | 7/1988 | PCT Int'l Appl. . |
| 88/06023 | 8/1988 | PCT Int'l Appl. . |
| US88/03564 | 10/1988 | PCT Int'l Appl. . |

OTHER PUBLICATIONS

Matthews et al., "The Thermal Effects of Skeletal Fixation-Pin Insertion in Bone," *The Journal of Bone and Joint Surgery*, 1984.
Turkel et al.-"A New and Simple Instrument for Administration of Fluids through the Bone Marrow," Reprinted from *War Medicine*, Apr. 1944, vol. 5, pp. 222-225.
Halvorsen et al.-"Evaluation of an Intraosseous Infusion Device for the Resuscitation of Hypovolemic Shock," *The Journal of Trauma*, Jun., 1990, vol. 30, No. 6, pp. 652-659.
"Disposable Intraosseous Infusion Needles," *Cook Critical Care Trade Journal*, 1990.
Pelt-"Infusion Needle Safe for Critically Ill Tots," *Insight*, Feb. 12, 1990, p. 52.
Lebow-"Intraosseous Needle Helps Save Children from SIDS and Shock," *Emergency Medicine News*, May 1990.
Zenk-"Therapy Consultation," *Clinical Pharmacy*, vol. 9, Feb. 1990, pp. 90-91.
Spivey-"Intraosseous Infusions," *The Journal of Pediatrics*, Nov. 1987, vol. 111, No. 5, pp. 639-643 and 443.
Plewa et al.-"Fat Embolism Following Intraosseous Infusion," *Annals of Emergency Medicine*, Apr. 1988.
Otto et al.-"Intraosseous Infusion of Fluids and Therapeutics," *Continuing Education Article* #3, vol. 11, No. 4, Apr. 1989, pp. 421-431.

*Primary Examiner*—John G. Weiss
*Assistant Examiner*—Jeffrey A. Smith
*Attorney, Agent, or Firm*—Arnold, White & Durkee

[57] ABSTRACT

A method and device for use in delivering or withdrawing fluid to or from the vascular system of bone marrow, wherein a tubular conduit is inserted into bone and fluid is delivered or withdrawn to or from a reservoir through a seal means surrounding a head attached to one end of the conduit in communication with bone marrow at the opposite end of the conduit. Access to bone marrow is achieved by implanting an improved intramedullary catheter of the present device within a bone and creating a reusable passage via a conduit placed between bone marrow and the outer surface of bone or skin.

23 Claims, 3 Drawing Sheets

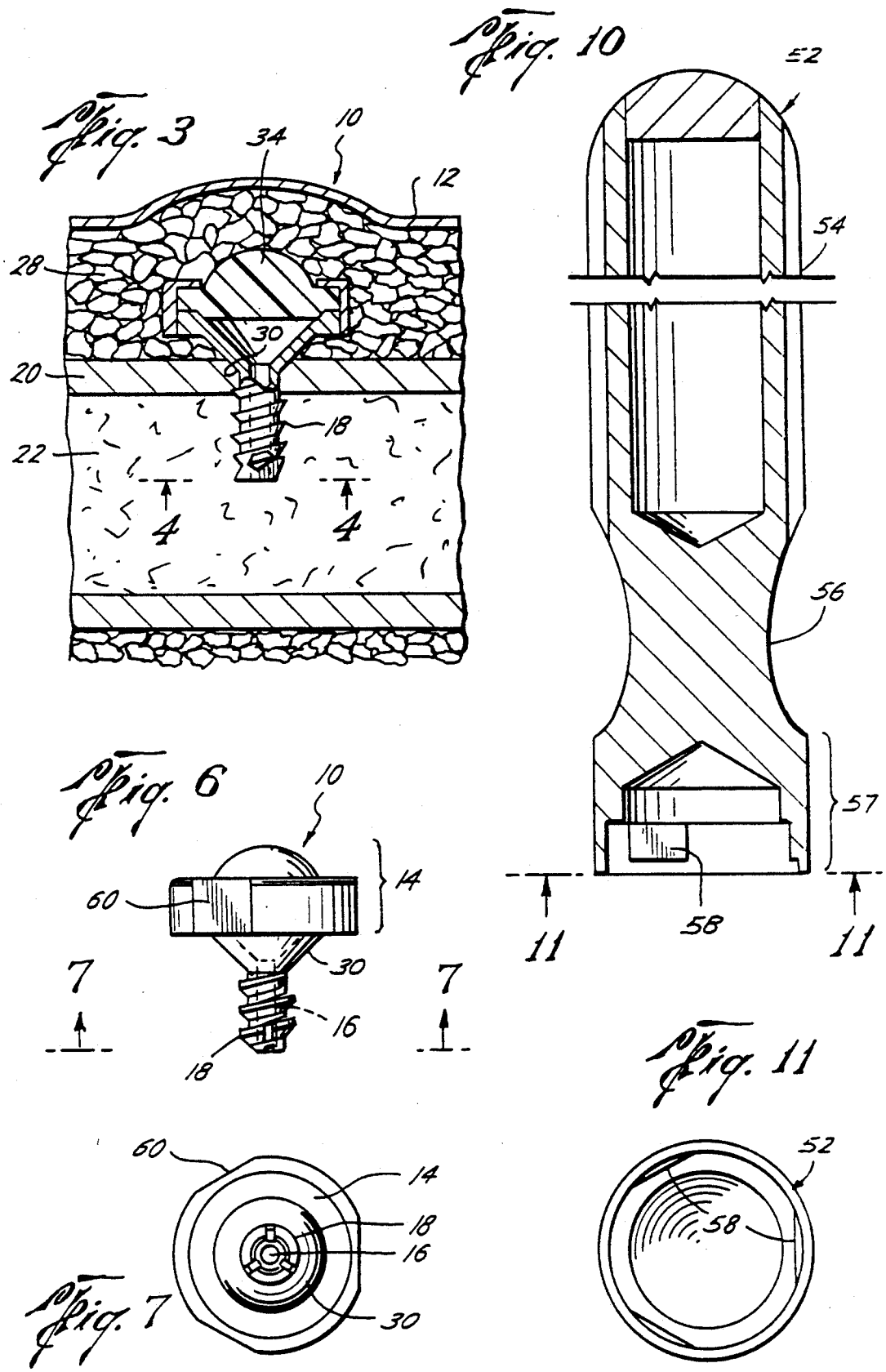

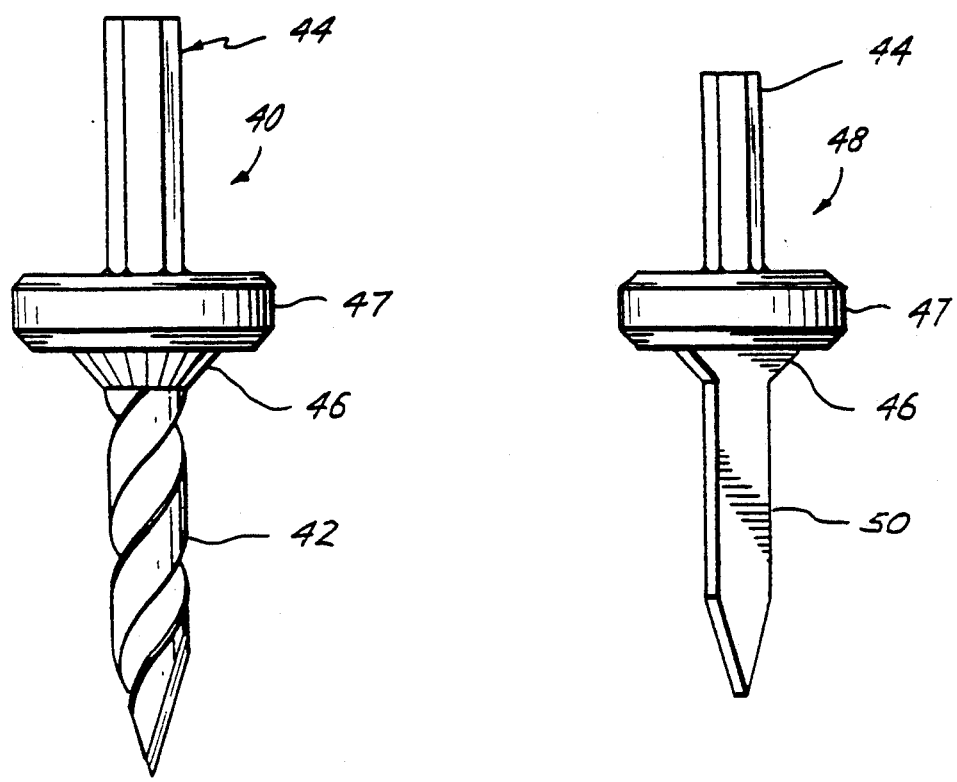

INTRAMEDULLARY CATHETER

This is a divisional of application Ser. No. 07/648,624, filed Feb. 1. 1991, now U.S. Pat. No. 5,122,114.

BACKGROUND OF THE INVENTION

This invention relates to an intramedullary catheter. More specifically, the present invention is directed toward an improved device and method for allowing repetitive delivery or withdrawal of fluids to or from the vascular system of bone marrow through a catheter device placed within a patient's bone.

Repetitive delivery of fluid into a patient's vascular system often entails an intravenous device. When a patient requires fluid during each of numerous treatment sessions, an intravenous device must be inserted into the patient's vein. Each time the device is inserted, the physician runs the risk of missing the vein and injecting fluid outside the vein. Moreover, physicians often find it difficult to find a vein, or once they do so, numerous injections into that vein may cause its rapid deterioration. In an effort to solve the above problems, numerous devices are commercially available which comprise a catheter commonly inserted into a large vein and having a self-sealing septum through which repetitive injections can be made into the catheter. Thus, instead of repetitively placing a needle into a vein, the needle can be repetitively placed through a septum and into a port attached to a conduit placed within the vein.

Intravenous catheters represent substantial improvements in the art, however, when used over a long period of time, they can cause infection and clotting in the vein near the area where the catheter is placed into the vein. Recently, a device and method were developed for repetitively placing fluid into the vascular system via bone marrow. Such a device incorporated herein as U.S. Pat. No. 4,772,261 comprises an intramedullary catheter placed into a tapped bore within the patient's bone and into the bone marrow. This device allows placement under the skin and the closing of the skin over the device such that the portion of the catheter extending outside the bone remains hidden under the skin. Although catheters placed into a patient's bone marrow represent improvements in the art, they are often difficult to place, and once in place, are difficult to find. It is important, when placing a bone catheter, that the head or outermost member of the catheter be large enough to be easily detectable (or palpable) by the physician so that he or she can target the injection needle into the septum of the catheter. Furthermore, it is important that once a catheter is in place, it be securely held within the bone marrow and will not cause pain during normal patient movement. It is also important that the catheter-bone interface be secure or tight enough so as not to leak fluid outside the bone and into the surrounding tissue. However, the base of the catheter must be designed or shaped not to cause necrosis of the underlying periosteum resulting in a nidus for infection. Still further, it is important that a device be provided for repetitive harvesting or withdrawing of fluid from bone marrow as well as repetitive delivery of fluid to bone marrow.

SUMMARY OF THE INVENTION

Accordingly, it is desirable to produce an improved intramedullary catheter which can be rapidly placed and securely held in a patient's bone. The improved catheter of the present invention can either be implanted underneath the patient's skin or can reside partially above the skin in a percutaneous embodiment. If implanted, the catheter is placed within a bore made through the patient's bone and into underlying bone marrow. A physician can feel for the catheter residing underneath the patient's skin and thereby insert a needle through the skin and into the catheter for delivery or withdrawal of fluid to or from the patient's vascular system. If the device is not implanted, but is placed percutaneous, the physician can simply visually detect the head of the catheter and gain access to the vascular system above the patient's skin.

The present invention includes a conduit having threads extending along the length of the catheter from a conically shaped head to a distal end that, when placed, resides within the patient's bone marrow. The threads act to securely hold the device within bone as the patient is undergoing normal activity. The improved device is securely held in the bone with a conically shaped head extending either inside (implanted) or outside (percutaneous) the patient's skin. If implanted, the conically shaped head allows sealing engagement with the bone adjacent the bore to prevent infection from entering the bone marrow and to prevent fluid from leaking outside the bone into the surrounding tissue.

In accordance with one embodiment of the present invention, a novel device is provided which can be implanted underneath a patient's skin. The implanted device is adapted to allow repetitive passing of fluid to a patient's vascular system via bone marrow. The implanted device comprises a tubular conduit with threads extending along the length of the conduit from a head placed at one end to the tip at the other end. By drilling a bore into the bone, the threaded conduit can be screwed into the bore by rotational movement of a tool placed over the head. When fully implanted into the bone, the tip of the conduit resides within the bone marrow of the bone and the head sealingly abuts the outer surface of the bone. A seal means is provided and adapted to retain a sealing membrane on the head of the device. The seal means includes a silicon elastomer which permits repetitive insertion and withdrawal of a needle without exposing bone marrow to infection. The head is generally conically-shaped having interior walls defining a saucer-shaped cavity covered by the seal means. The cavity is of sufficient size to receive a needle tip and allow a fluid access reservoir between the needle tip and the conduit (and subsequently the bone marrow). The seal means, or port to the septum, is of sufficient size to be easily detected by the physician when placing the needle in the implanted head. Although a physician cannot see the implanted device, he or she can target the needle by feeling for the underlying head and sealing membrane. The sealing membrane is dome shaped to aid the physician in palpably detecting the target area.

In accordance with another embodiment of the present invention, there is provided a device which is only partially implanted. The head portion of the device remains outside the patient's skin in a percutaneous embodiment. The percutaneous device is similar to the implanted device in that it has threads on the outside of a conduit extending from a conically shaped head to the distal tip. However, unlike the implanted device, the percutaneous device can be inserted directly into the bone without having to first drill a bore into the bone. The percutaneous conduit having cutting threads placed along the outer surface of the conduit and a cutting tip at the distal tip of the threads. The threaded conduit is screwed into bone by rotating a tool placed over the head of the device. As the device is being screwed into the bone, cutting tip and cutting threads form a bore simultaneous with the insertion of the device. Thus, the percutaneous device can be placed directly into the bone without having to pre-drill a bore as in the implanted embodiment. Placement of the percutaneous device is therefore quickly performed to allow emergency delivery or withdrawal of fluid to or from the patient's bone marrow.

In either the implanted or percutaneous embodiments, sealing engagement is made with the bone to prevent infection from entering the bone marrow and to prevent fluid from leaking from the bore. If implanted, the conically shaped portion of the head sealingly abuts the bone surface adjacent the bore. Thus, infection is prevented from entering the bore between the head and the bone surface. Conversely, if the head is configured above the patient's skin as in the percutaneous embodiment, a butting member or protrusion sealing abuts the bone surface to prevent infection from entering the bore. Thus, as is shown here and throughout the following discussion, both embodiments have provisions which prevent infection from entering the bone marrow while also preventing fluid leakage from the bore. Prevention of infection and leakage is provided by a combination of the conically shaped, sealing portion of the head as well as the sealing membrane which covers the head. Furthermore, the threads are radially dimensioned to provide a relatively tight fit with the bore such that little or no passage exists between the bone marrow and the outside air or overlying tissue.

In accordance with the instant invention, there is also provided a novel method of passing fluid to and from the vascular system of a patient through bone. The method includes placing an implanted device underneath the skin in communication with the patient's bone marrow. Once placed, passage of fluid through the device and overlying skin is easily achieved by placing a needle into the device and injecting or withdrawing fluid therethrough. The method comprises the steps of providing a device having an elongated, tubular conduit with threads extending the length of the conduit; drilling a bore into the bone; implanting the device into the bore with the conduit in operable communication with the bone marrow; injecting fluid through the elastomer and into the conduit for delivery through the conduit into the bone marrow and transport to the vascular system; repeating the injecting step for repetitive delivery of fluid to the vascular system; withdrawing fluid through the elastomer from the bone marrow; and, repeating the withdrawing step for repetitive, relatively long-term drawing of fluid from the patient's vascular system. The drilling step comprises making the bore of sufficient diameter to receive and securely hold the threads of the conduit. The implanting step comprises forming mating threads to the bore in response to rotating movement of the conduit within the bore. The drilling step comprises drilling the bore extending from the surface of the bone to the bone marrow, or extending from the skin covering the bone to the bone marrow. The implanting step comprises rotatable insertion and sealing a small portion of the outer surface of the head against the surface of the bone to prevent infection from entering the bore between the outer surface of the head and the surface of the bone.

In accordance with the instant invention, there is also provided a novel method of passing fluid to or from the bone marrow wherein the head of the device is not implanted underneath the skin. In this percutaneous embodiment, a device is provided with cutting threads extending the length of the conduit with a cutting tip attached to the distal end of the conduit and a head attached to the proximal end. An elongated tool is placed over the head and the tool is rotated such that the cutting tip and threads form a bore directly into the bone simultaneous with the placement of the device within the bone. Upon full insertion of the device, a needle can be placed through the sealing membrane to pass fluid to or from the bone marrow. Moreover, when the device is fully inserted, a protrusion placed on the conduit sealingly abuts the outer surface of the bone to prevent infection from entering the bore while also preventing fluid from exiting the bore. It is important to note that a bore need not be pre-drilled when using the percutaneous device since the percutaneous conduit is similar in function to a drill bit. By attaching the rotating tool to the distal end and screwing the device into the bone, the device functions as both a catheter and drill bit for simultaneous placement within the bone.

If, for aesthetic reasons or for a desire to decrease the exposure of subcutaneous tissue to infection, the device is implanted beneath the skin, then a pilot bore must be predrilled. A drill bit is provided having a cutting shaft with a cutting or piercing tip placed at one end and a countersink attached near the other end. The tip is sharp to ensure precise placement of the bore within the bone. Moreover, the cutting shaft increases in diameter from the tip to provide a smooth bore which is countersunk at the bone surface by the countersink attached to the cutting shaft. The countersink produces a pilot bore entrance having a conical shape which matches the conically shaped head such that a fairly precise and smooth fit exists between the countersink bore and the head. The matching of the countersink bore and the head prevents contamination or leakage therebetween. Collinear with the axis of rotation of the cutting shaft and attached to the countersink is a coupling shaft which can accommodate a rotating means such as a drill. Rotational movement provided by the drill will impart rotational cutting movement upon the cutting shaft and tip.

It is further appreciated that the present invention, including the conduit, head, threads, etc. can be coated or impregnated on the inside and/or outside with certain materials which can promote or inhibit certain biological characteristics. For example, Heparin bearing material may be placed on the inner surface of the conduit and saucer cavity to help prevent clotting within the fluid passage. Also, e.g., Titanium oxide can be placed on the outer surface of the buttress threads and head to promote fixation of the present device to the bone to further secure it to the bone and help prevent fluid leakage. Antibiotics may be placed on the inner and/or outer surface to prevent infection. Still further, proteins may be placed on the distal end of the conduit to prevent new bone or tissue formation on said tip which could occlude the conduit. It is understood that any of these materials can be either coated onto or impregnated directly into the inner or outer surface of the present device without departing from the scope and spirit of the present invention.

BRIEF DESCRIPTION OF THE DRAWINGS

FIG. 3 is a cross-sectional view of the implanted, adult-sized intramedullary catheter of the present invention secured within bone and extending entirely beneath the patient's skin.

FIG. 6 is a perspective view of the assembled, pediatric-sized intramedullary catheter of the present invention.

FIG. 7 is a bottom plan view along plane 7—7 from FIG. 6.

FIG. 8 is a perspective view of a twist drill bit used to produce a bore within bone through which the implanted intramedullary catheter of the present invention is installed.

FIG. 9 is a perspective view of a paddle drill bit used to produce a bore within bone through which the implanted intramedullary catheter of the present invention is installed.

FIG. 10 is a cross-sectional view of a rotating tool for engaging the intramedullary catheter of the present invention.

FIG. 11 is a cross-sectional view along plane 11—11 from FIG. 10.

DETAILED DESCRIPTION OF THE PREFERRED EMBODIMENTS

Figure 1:
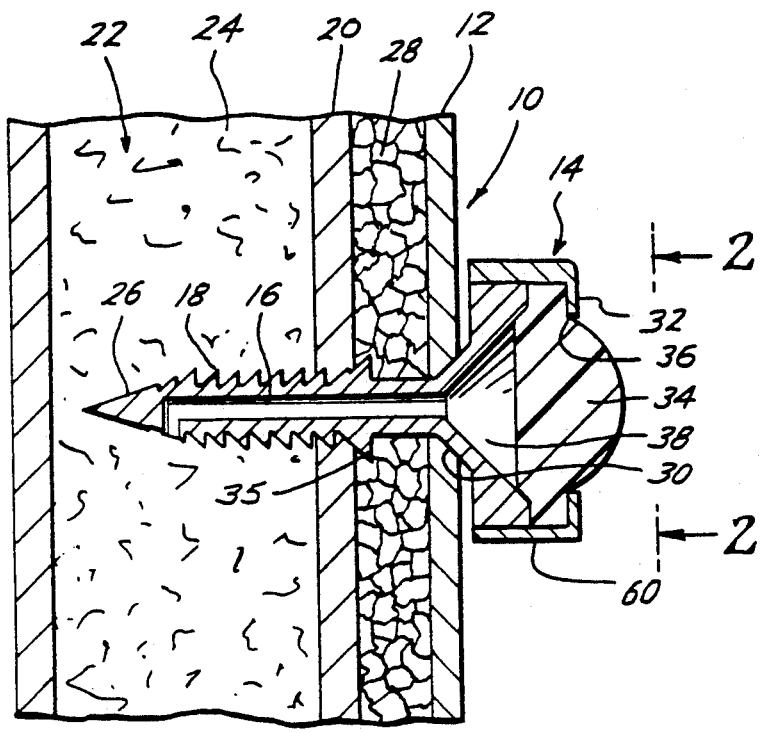
FIG. 1 is a cross-sectional view of the percutaneous intramedullary catheter of the present invention secured within bone and extending partially above the patient's skin.

Referring to the drawings, FIG. 1 illustrates a cross-sectional view of the improved intramedullary catheter 10 partially implanted beneath a patient's skin 12. The implanted device 10 shows head 14 extending above the skin and conduit 16 extending beneath the skin. The device is securely held in place by threads 18 placed along conduit 16 and engaged with cortical bone 20 and cancellous bone 22. Contained within cancellous bone 22 are spongy bony networks filled with venous sinusoidal spaces which forms bone marrow 24.

The embodiment shown in FIG. 1 illustrates device 10 having a catheter placed through skin 12 in a percutaneous arrangement. A physician can insert catheter 10 through the skin and directly into underlying bone. The distal tip 26 is designed to have one or more cutting edges for piercing subcutaneous tissue 28 and underlying bone 20 and 22. As tip 26 enters the bone similar to a drill bit entering a solid medium, threads 18 further cut the bone as conduit 16 enters the passage formed by tip 26 and threads 18. Once tip 26 penetrates the more dense cortical bone 20, threads 18 become seated in cortical bone 20 thereby allowing for easier penetration of tip 26 into the less dense cancellous bone 22. After device 10 is sufficiently screwed into bone 20 and 22, tip 26 will reside within the cancellous portion of bone 22 in communication with bone marrow 24. Moreover, when fully inserted, head 14, having a conical portion 30, will abut the outer surface of skin 12. Conical portion 30 will engage with the outer surface of skin 12, leaving a small gap between the major portion of head 14 and skin 12. Such a gap is important to prevent entrapment of bacteria between the head and skin. Furthermore, conical portion 30 functions to seal against the skin and prevent infection from entering subcutaneous tissue 28 via the outside environment. Also, conical portion 30 maintains elevation of head 14 above skin 12. The percutaneous configuration of FIG. 1 allows a physician to quickly insert device 10 through skin 12 and into underlying bone 20 and 22 without the necessity of pre-drilling a pilot hole or bore. Device 10, having cutting threads 18, functions as a drill bit for simultaneous drilling and placement of conduit 16 into underlying bone 20 and 22. When fully inserted, conical portion 30 of head 14 provides a seal thereby preventing infection from entering subcutaneous tissue 28 and/or marrow 24 between skin 12 and head 14. A radially extending protrusion 35 of conical shape at the proximal end of the threaded conduit acts as a sealing "stop" to prevent the catheter from being further advanced into the bone. Moreover, protrusion 35, being of larger radial dimension than threads 18, provides a seal against leakage of medications or fluids from the intramedullary space to outside the bone. Thus, protrusion 35 prevents medications or fluids from seeping from marrow 24 to subcutaneous tissue 28.

The importance of the percutaneous application of the present invention shown in FIG. 1 is further appreciated by physicians in the field. Often, in emergency situations, it is desirable to set forth immediate fluid delivery or withdrawal procedures to or from the patient's vascular system. In doing so, many physicians, in their haste, prefer the intravenous route since access to a vein is quicker and easier than access to bone marrow. However, as shown in the present invention, emergency access to bone marrow can be quickly achieved by the percutaneous embodiment. Device 10 can be quickly screwed into bone 20 and 22 in a one step procedure leaving head 14 exposed. Not only can device 10 be quickly inserted, but repetitive, subsequent fluid delivery or withdrawal can be achieved without having to continually enter a vein as in conventional art. Device 10 remains in place after emergency insertion for repetitive delivery or withdrawal of fluid to and from the patient's vascular system without incurring the disadvantages found in intravenous delivery systems.

Figure 2:
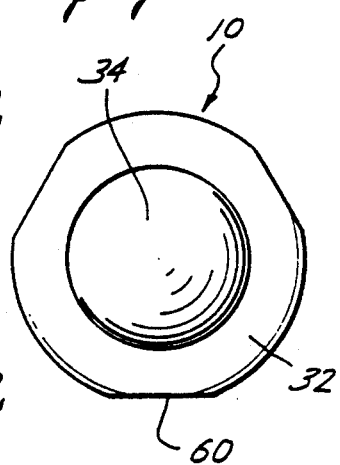
FIG. 2 is a top plan view of the present invention along plane 2—2 from FIG. 1.

FIG. 2 illustrates a top plan view of head 14 shown along plane 2—2 from FIG. 1. The outer portion of head 14 is shown having a substantially circular body 32, preferably stainless steel, plastic, titanium, etc. used to encompass a sealing membrane 34. As shown in FIGS. 1 and 2, membrane 34 is dome-shaped on the exposed outer surface to enable a physician, nurse, or patient to easily palpate the location of septum or membrane 34. This is important so that a needle can be accurately inserted into membrane 34 with less chance of misguiding the needle and injecting fluid outside of device 10. Conventional intravenous catheters utilize a membrane or septum of the present invention, but do not have a palpable, easily detectable dome-shaped membrane or septum of the present invention. Often, in intravenous catheters, a physician may have to insert a needle many times in order to successfully find and/or enter the device port.

By being dome-shaped and having sufficient radial dimension, membrane 34 is easily located and quickly accessed by a physician. The diameter of membrane 34 must be large enough to provide an adequate target, but not so large as to cause discomfort or unsightliness. Preferably, the diameter of the domed portion of membrane 34 is approximately 12 mm in an adult and 10 mm in a pediatric model. It is found by the Applicant that such a preferred size provides good target area for physicians to access device 10. However, diameter of membrane 34 can vary substantially without deviating from the scope of this invention.

FIG. 3 illustrates another embodiment showing device 10 fully implanted beneath skin 12. In circumstances where it is not essential that device 10 be placed immediately, device 10 can be implanted under the skin to provide a more aesthetic appearance and to further protect the body from the possibility of infection entering subcutaneous tissue 28. Depending upon the depth of tissue 28, device 10 once secured in place will allow varying degrees of palpability. If tissue is relatively shallow, the dome-shaped portion of membrane 34 protrudes against skin 12 or tissue 28 and beyond the plane of skin 12. Thus, in shallow-tissue areas, the dome-shaped membrane 34 is visually detected by the physician to enable insertion of a needle into the membrane. However, in areas where subcutaneous tissue 28 is relatively deep, palpable detection is easily achieved due to the large radial dimensions of head 14. It is understood that either embodiment, implanted or percutaneous, allows the physician to easily pass fluid to and from the bone marrow vascular system.

Illustrated in FIG. 3 is conical portion 30 which sealingly abuts against the outer surface of cortical bone 20. In addition to providing sealing arrangement, conical portion 30 is dimensioned to slightly elevate head 14 above the outside surface of bone 20 such that only a small portion of the inside surface of head 14 touches bone 20. Pain during normal movement is minimized by having only a small portion of head 14 pressing on the nerve-rich periosteum. Furthermore, minimizing the contact area between head 14 and the surface of bone 20 allows normal circulation of the periosteum under the head thereby preventing substantial cell death and necrosis. Thus, when fully inserted and implanted underneath a patient's skin 12, device 10 is configured to prevent infection from entering bone marrow from either the outside environment or tissue 28 overlying bone 22. Membrane 34 and conical portion 30 ensure such infections from happening. Further, membrane 34 and conical portion 30 prevent fluid from leaking from underlying bone marrow 24 to tissue 28.

Shown in FIG. 3 is the distal end of conduit 16 which includes self-tapping threads. Self-tapping threads may be notched in a tetrahedral shape at the distal point thus permitting maximum cutting through cancellous bone 22. The self-tapping feature is advantageous in that it will save a step in the implantation procedure and will make it simpler and faster to insert device 10 into bone 20 and 22. Instead of having to tap threads into the bore, the self-tapping threads can make their own threads as threaded conduit 16 is screwed into the pre-drilled bore. The implanted device 10 requires only that a bore be drilled and that threads can be made within the bore by the self-tapping feature of threads 18. It is important to note that although self-tapping threads shown in FIGS. 3 and 4 utilize a tetrahedral design, any standard self-tapping design can be used, which may also include but is not limited to a three-point notch design shown in FIG. 7.

Figure 5:
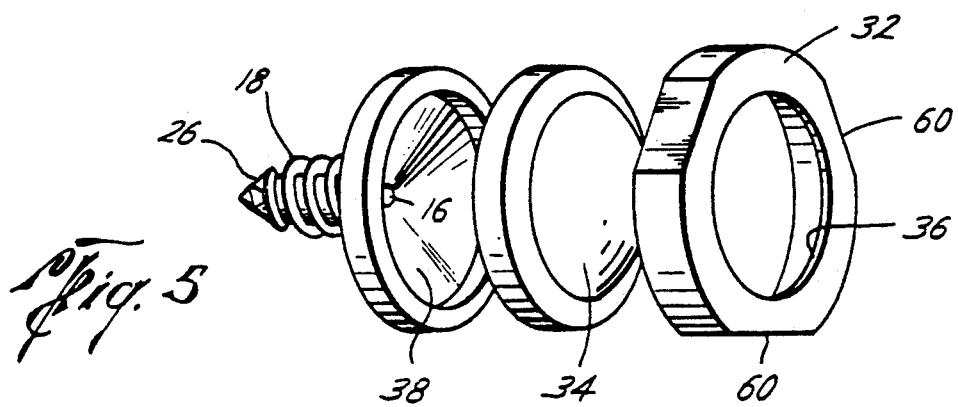
FIG. 5 is a perspective view of the disassembled intramedullary catheter of the present invention.

As shown in FIGS. 1, 3, and 5, threads 18 which are self-tapping, provide quick and secure implantation of device 10 within bone 20 and 22. Buttress threads can be used, and are often called ASNIS cancellous bone threads commonly found in the orthopedic industry. The threads are preferably ten pitch, or 2.5 mm per revolution and measure 6.5 mm at the crest and 4.0 mm at the root (basic shaft diameter). The inside diameter of conduit 16 is preferably 13 gauge or 2.4 mm. Buttress threads are useful in withstanding uni-directional stress and have nearly ten times the holding power (pull-out strength and tightening torque) than standard machine threads placed in bone. Furthermore, 13 gauge conduit provides a generous size that is more than adequate for the infusion of fluids and medications or for the aspiration of blood and marrow. Thus, not only is it important that the inside diameter of conduit 16 be sufficiently large to carry fluid, but it must also be sufficiently dimensioned to carry marrow if device 10 is used for repeated bone marrow harvesting. Bone marrow harvesting, useful in bone marrow transplants and/or monitoring of the bone marrow, is achieved by aspirating through membrane 34 blood, fluids or particulate matter from bone marrow 24. In applications wherein medications can suppress the bone marrow or in patients with immune deficiency disease, or who require frequent monitoring of bone marrow activity, the present invention provides a useful technique for correctly withdrawing portions of the patient's bone marrow. In addition, the bone marrow may be repeatedly harvested for the determination of complete blood counts and all routine blood chemistries without the necessity of having to access the vein.

FIG. 5 is a perspective view of various components of device 10. Membrane 34 is sealed between body 32 and conical portion 30. The inside surface of body 32 is circular to surround the outer perimeter of membrane 34. In addition, body 32 includes a lip 36 which engages membrane 34 against the outer surface of conical portion 30 when assembled. After device 10 is assembled, the dome portion of membrane 34 protrudes through the circular opening within body 32. The inner portion of head 30, which underlies membrane 34, forms a reservoir or cavity defined by saucer 38. The reservoir or cavity is of sufficient size to accommodate the tip of a needle inserted through membrane 34. If fluid is injected from the needle into the cavity, it is forced into the inner passage of conduit 16. Membrane 34 permits repeated access of a needle to the reservoir such that when the needle is withdrawn, the hole created by the needle is sealed to prevent infection from entering the reservoir. The dome-shaped portion of membrane 34 and the reservoir are of sufficient size to accommodate successful introduction of a needle from a wide range of angles. The floor of the reservoir is saucer-shaped to direct the needle towards the conduit 16.

Figure 4:
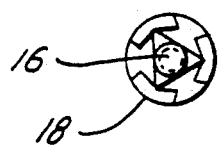
FIG. 4 is a sectional view of the present invention along plane 4—4 from FIG. 3.

FIG. 6 illustrates another embodiment of self-tapping threads having a three-point notch design rather than the tetrahedral design shown in FIGS. 3 and 4. Applicants have found that the notch design provides good self-tapping characteristics in cortical bone. Also, FIG. 6 illustrates device 10 of smaller dimensions, i.e., having a radially smaller head 14 and shorter conduit 16 to accommodate pediatric/small bone application. Smaller catheters are designed primarily to accommodate the smaller size bones found in pediatric population and in small animals weighing approximately 30–90 pounds. The length of conduit usable in smaller-bone applications can vary drastically, however, 9 mm being a preferred size. A 9 mm tip will usually allow the distal end of conduit 16 to enter marrow 24 without impinging on the opposite wall or perforating through the opposite side of cortical bone 20. It is understood, however, that conduit 16 can be of any dimension (length or width) depending upon the particular bone size and/or fluid delivery rate. If a bone is relatively large, then longer catheters are preferred. Conversely, if a bone is relatively small, then a smaller catheter with a shorter conduit is preferred. In either case, the optimal length of catheter is chosen such that the distal end resides within marrow 24 and somewhere between the opposing walls of cortical bone 20.

It is further appreciated that the present device 10, including the conduit 16, head 14, tip 26, threads 18, conical portion 30, body 32, lip 36 and saucer 38 can be coated or impregnated on the inside and/or outside with certain materials which can promote or inhibit certain biological characteristics. For example, Heparin bearing material may be placed on the inner surface of the conduit 16 and saucer cavity 38 to help prevent clotting within the fluid passage. Also, e.g., Titanium oxide can be placed on the outer surface of conduit 16, buttress threads 18, head 14 and tip 26 to promote fixation of the present device to the bone to further secure it to the bone and help prevent fluid leakage. Antibiotics may be placed on the inner and/or outer surface of conduit 16, head 14, threads 18, etc to help prevent infection. Still further, proteins may be placed on the distal end of conduit 16 or tip 26 to prevent new bone or tissue formation on said tip which could occlude the conduit. It is understood that any of these materials can be either coated onto or impregnated into the inner or outer surface of selective portions of the present device 10 without departing from the scope and spirit of the present invention.

FIG. 7 illustrates a bottom plan view along plane 7-7 from FIG. 6. Self-tapping threads 30 are shown with the three-point notch design typically used for implantation with cortical bone. Also shown is conical portion 30 extending radially outward from conduit 16 toward the underneath side of head 14. The outer portion of conical section 30 is understood to engage against skin 12 (in the percutaneous embodiment) or bone 14 (in the implanted embodiment) to provide a sealing arrangement necessary to prevent infection or fluid leakage.

FIG. 8 illustrates a dedicated drill bit 40 specifically used for the implanted embodiment. Bit 40 serves to bore the proper size hole for optimum fitting of the device's self-tapping threads 18 into bone 20 and 22. Twist drill bit 40 comprises an elongated cutting shaft 42 having spiral cutting edges which cut and remove cortical and cancellous bone 20 and 22, respectively, in response to rotational movement placed upon shaft 44. As the cutting shaft 42 forms a bore within bone 20 and 22, a collar 47 functions to stop the drilling at the proper depth so as not to drill completely through the bone and out the other side. Thus, collar 47 prevents the distal tip of cutting shaft 42 from penetrating the opposite wall or through the opposite wall. Countersink 46, functions to create the proper angle of the bone onto which the conical portion of the head can seat and form a tight seal. Without this countersinking step, the process of making threads, either with a tap or with the self-tapping threads, may damage the entrance into the bone to where it may leak fluid from the bone marrow and into the surrounding tissue. The countersink dresses the bone in a smooth circular fashion to promote a sealing fit. In addition, if the countersinking step takes place separate from the drilling, the angle of the countersink may be different from the angle of the bore, again causing an irregularity with respect to device 10, which provides a space for leaking. Shaft 44, shown at the top of twist drill bit 40, is of standard size to accommodate a drill such that rotational movement of a drill will impart rotational movement to shaft 44 and consequently to cutting shaft 42. Shown in FIG. 9 is paddle drill bit 48 having a planar cutting shaft 50 extending between the distal tip of bit 48 and countersink 46. Attached to the opposite side of countersink 46 and collinear with the axis of rotation of shaft 50 is shaft 44 onto which a standard drill can be attached. Similar to twist drill bit 40, paddle drill bit 48 is used to produce a bore from the outer surface of cortical bone 20 through both cortical bone 20 and cancellous bone 22. Either twist bit 40 or paddle bit 48 can be used to form the bore.

FIG. 10 illustrates a device driver or tool 52 useful for inserting device 10 either within a bore as in the implanted embodiment, or directly through the bone as in the one-step percutaneous embodiment. Tool 52 includes a handle 54, a neck 56 and a head 57. Placed within head 57 are keys or sockets 58 which engage with the flat, planar sections 60 made within the circumference of head 14. FIGS. 2, 5 and 7 illustrate flat, planar sections 60 placed in head 14. The purpose of planar sections 60 is to provide a flat surface adapted for receiving keys 58 such that rotational movement upon handle 54 can be transferred to device 10. The advantages in having flat, planar sections 60 is that there are no grooves or crevices on head 14 which can trap bacteria and does not cause interference with overlying tissue when implanted beneath the skin. By engaging keys 58 with planar sections 60 and then rotating the handle 54, device 10 is screwed into bone 20 and 22. Handle 54 may be in the shape of a standard screw driver handle or standard orthopedic instrument handle with keys 58 accommodating head 14 much like a socket wrench engages a nut. Tool design has the benefit of securely holding device 10 so that alignment is easily made with the pilot hole or bore. Furthermore, the smooth outer circumference of head 14 protects the surrounding tissue during insertion. Tool 52 is relatively simple and easy to use. Twisting motion upon handle 54 will provide necessary rotation and insertion of device 10 within the bore. Upon full insertion, rotation will cease and tool 52 is quickly and easily withdrawn. FIG. 11 illustrates grooves 58 placed within tool 52.

The foregoing description of the invention has been directed to two preferred embodiments of the present invention. One embodiment being percutaneous and the other being implanted. It will be apparent, however, to those skilled in the art that modifications in both apparatus and method of either embodiment may be made without departing from the spirit and scope of the invention. For example, it is understood that the present invention can be implanted either partially above or totally below a patient's skin—in accordance with either embodiment. Also, the present invention can be used for repetitive delivery or withdrawal of fluid and small particles to or from bone marrow. Further, it is understood that buttress threads may be used for securing the invention within bone or a bore contained in bone. Although buttress threads are preferred, other securing means or types of thread may be used without departing from the invention. Further, the present invention uses various forms of self-tapping threads which alleviate the need for tapping the bore prior to insertion of device 10. Any form of self-tapping arrangement, including, but not limited to, the tetrahedral or three-point design can be used without departing from the invention. Still further, it is understood that conduit 16 and head 14 may be sized to accommodate any particular bone size or shape. Therefore, it is Applicants' intention in the following claims to cover all such equivalent modifications and variations which fall within the true spirit and scope of the invention.

What is claimed is:

1. A device for passing fluid through bone, comprising:
   an elongated tubular conduit insertable into said bone and having a distal end and a proximal end with threads extending along said conduit from said distal end to said proximal end;
   a conical head attached to the proximal end of said conduit, said head having an internal saucer cavity for receiving a needle placed therein;
   rotating means releasably attachable to said head for inserting said distal end through said bone and into underlying bone marrow; and
   seal means adapted to retain a sealing member on said head and over said cavity for permitting repetitive insertion of said needle through said sealing member and into said cavity to pass fluid between said needle and said bone marrow, and to seal the conduit after withdrawal of the needle to prevent infection from entering the bone marrow.

2. The device as recited in claim 1, wherein said seal means comprises an elastomer configured to repetitively receive said needle for delivering fluid from said needle and into said marrow.

3. The device as recited in claim 1, wherein said seal means comprises an elastomer configured to repetitively receive said needle for withdrawing fluid from said marrow and into said needle.

4. The device as recited in claim 1, wherein the device further comprises a material to inhibit blood clotting.

5. The device as recited in claim 1, wherein the device further comprises an antibiotic material to prevent infection.

6. The device as recited in claim 1, wherein the device further comprises a protein material to prevent new bone or tissue formation.

7. The device as recited in claim 1, wherein said conduit and said head comprising titanium oxide coating placed on the outside surface.

8. The device as recited in claim 1, wherein said head is implanted underneath a patient's skin with the outer surface of said head adapted to sealingly butt against the outer surface of said bone adjacent said bore when said distal end is fully extended into said bone marrow.

9. The device as recited in claim 8, wherein said conically shaped outer surface is configured to prevent infection from entering the bore and to prevent fluid from leaking from the bore.

10. The device as recited in claim 1, wherein said device further comprises:
    a head having a conically shaped outer surface adapted to butt against the surface of skin overlying said bone adjacent said bore when said distal end is fully inserted into said bone marrow;
    a converging cutting tip attached to the distal end of said conduit to form a bore through which said conduit will reside when said device is rotatably inserted; and
    means placed on the conduit for sealingly butting against the surface of said bone adjacent said bore when said distal end is fully extended into said bone marrow.

11. The device as recited in claim 10, wherein said butting means includes a conical protrusion extending outward from said conduit near the surface of said bone when said conduit is fully inserted to prevent infection from entering the bore and to prevent fluid from leaking from the bore.

12. The device as recited in claim 1, wherein said conduit and said head have a coating placed on the outside surface of said conduit and said head to promote fixation to said bone and substantially enhance new growth of bone at the junction between the outside surface and said bone.

13. A device adapted for passing fluid to and from a patient's bone marrow, comprising:
    an elongated tubular conduit having a distal end and a proximal end with self-tapping, buttress threads extending along the outer surface of said conduit from said distal end to said proximal end;
    a converging, cutting tip attached to said distal end;
    a head having opposed conically shaped first side and saucer shaped second side, said conically shaped first side attached to the proximal end of said conduit;
    rotating means attachable to said head for rotatably inserting said cutting tip into said bone to form a bore through which said distal end is placed within said bone marrow and said first side is placed against the surface of skin overlying said bone when said conduit is fully inserted;
    means placed on the conduit to sealingly butt against the surface of said bone adjacent said bore when said distal end is fully inserted into said bone marrow; and
    seal means adapted to retain a silicone elastomer on said second side for permitting repetitive insertion of a needle through said elastomer and into said saucer to pass fluid to and from the conduit for transport to and from said bone marrow, said seal means also adapted for sealing the conduit after withdrawal of the needle to prevent infection from entering the bone marrow.

14. The device as recited in claim 13, wherein said seal means comprises an elastomer configured to repetitively receive said needle for delivering fluid from said needle and into said marrow.

15. The device as recited in claim 13, wherein said butting means includes a conical protrusion extending outward from said conduit near the surface of said bone to prevent infection from entering the bore and to prevent fluid from leaking from the bore when said conduit is fully inserted.

16. The device as recited in claim 13, wherein said rotating means further comprises:
    a plurality of surfaces arranged around the outer perimeter of said head; and
    a tool for engaging said surfaces for screwing the conduit into said bore.

17. The device as recited in claim 13, wherein said seal means comprises an elastomer configured to repetitively receive said needle for withdrawing fluid from said marrow and into said needle.

18. The device as recited in claim 13, wherein the device further comprises a material to inhibit blood clotting.

19. The device as recited in claim 13, wherein the device further comprises an antibiotic material to prevent infection.

20. The device as recited in claim 13, wherein the device further comprises a protein material to prevent new bone or tissue formation.

21. The device as recited in claim 13, wherein said conduit and said head have a coating placed on the outside surface of said conduit and said head to promote fixation to said bone and substantially enhance new growth of bone at the junction between the outside surface and said bone.

22. The device as recited in claim 13, wherein said first side comprises a cone-shaped, exterior body converging at an angle radially inward from an outer circumference of said head to the outer surface of the proximal end of said conduit.

23. The device as recited in claim 22, wherein said cone-shaped exterior body is adapted to butt against the skin when said distal end is fully extended to prevent infection from entering the bore created through the skin.

* * * * *